United States Patent [19]

Chang et al.

[11] Patent Number: 4,775,679

[45] Date of Patent: Oct. 4, 1988

[54] CERTAIN HETEROCYCLIC-ETHYL-2,3-DIHYDROBENZOFURANS USEFUL AS ANTI-INFLAMMATORY AGENTS

[75] Inventors: Michael N. Chang, Westfield; David A. Boulton, Edison; Kathryn L. Thompson, Westfield, all of N.J.

[73] Assignee: Merck & Co., Inc., Rahway, N.J.

[21] Appl. No.: 45,651

[22] Filed: May 4, 1987

Related U.S. Application Data

[62] Division of Ser. No. 727,317, Apr. 25, 1985, Pat. No. 4,713,393.

[51] Int. Cl.$^4$ .................. A61K 31/415; C07D 405/06
[52] U.S. Cl. ........................... 514/397; 514/382; 514/422; 514/443; 514/444; 514/469; 548/251; 548/252; 548/253; 548/336; 548/525; 549/57; 549/51; 549/58; 549/60; 549/463; 549/470; 549/471

[58] Field of Search ............... 549/60, 51, 57, 58, 549/463, 470, 471; 548/336, 251, 252, 253, 525; 514/397, 444, 382, 422, 443, 469

[56] References Cited

U.S. PATENT DOCUMENTS

4,490,531 12/1984 Johnson .................... 546/269
4,495,357 1/1985 Johnson .................... 546/269

Primary Examiner—Mary C. Lee
Assistant Examiner—Bernard I. Dentz
Attorney, Agent, or Firm—Theresa Y. Cheng; Michael C. Sudol

[57] ABSTRACT

Phenylalkyl-2,3-dihydrobenzofurans and analogs were prepared by (1) nucleophilic substitution involving an appropriately substituted 2,3-dihydrobenzofuranol (or 2,3-dihydrobenzopyranol) and a cinnamylhalide followed by reduction; or (2) by Wittig reaction involving a halomethyl derivative of 2,3-dihydrobenzofuran (or 2,3-dihydrobenzopyran and an aryl or a heteroaryl aldehyde followed by reduction. These compounds were found to be potent anti-inflammatory agents.

9 Claims, No Drawings

CERTAIN HETEROCYCLIC-ETHYL-2,3-DIHYDROBENZOFURANS USEFUL AS ANTI-INFLAMMATORY AGENTS

This is a division of application Ser. No. 727,317, filed 4/25/85 new U.S. Pat. No. 4,713,393.

BACKGROUND OF THE INVENTION

The present invention relates to novel phenylalkyl-2,3-dihydrobenzofurans and the corresponding dihydrobenzopyrans useful as anti-inflammatory agents. A group of benzyldihydrobenzofurans have been disclosed in U.S. Pat. No. 4,435,422 as effective diuretic agents. However, this patent does not disclose the novel compounds of the present invention, nor does it disclose the anti-inflammatory activity of the compounds of the present invention.

The novel compounds are effective in vitro as both leukotriene and prostaglandin synthesis inhibitors in the peritoneal macrophage assay and the polymorphonuclear leukocyte assay. They are also potent lipoxygenase inhibitors. Furthermore, they are found to be active in vivo in the topical mouse ear assay and the U.V. erythema assay as topical anti-inflammatory agents.

Recent studies demonstrated that macrophages and PMNs participate in the development and progression of chronic inflammatory diseases such as rheumatoid arthritis. During the progression of inflammatory conditions, there is generally an appearance and/or presence of macrophages and lymphocytes, especially macrophages and polymorphonuclear leukocytes. Macrophages are known to secrete various products in response to inflammatory stimuli. For example:

(1) Neutral proteinases—the destructive peptide bond cleaving enzyme which has been shown to be directly involved in rheumatoid cartilage destruction; and (2) Prostaglandins (PG) (e.g., $E_2$ and $I_2$ by mouse peritoneal macrophages) and other arachidonic acid derivatives derived from both the cyclooxygenase and the lipoxygenase pathways.

These archidonic acid oxygenation products have been identified as the critical mediators of various acute inflammatory conditions.

Accordingly, pharmacological agents which are capable of inhibiting the formation of, the release of a mediator from, or the function of macrophages or polymorphonuclear leukocytes may also be effective agents in the treatment of rheumatoid arthritis, emphysema, bronchial inflammation, asthma, osteoarthritis, acute respiratory distress syndrome, shock syndromes, e.g., endotoxin shock syndrome, spondylitis, lupus, gout, psoriasis, pain, eye inflammation, and other inflammatory diseases.

Regarding the topical mouse ear assay, it has been previously established that classical nonsteroidal anti-inflammatory agents such as indomethacin and steroidal anti-inflammatory agents such as dexamethasone are active in this assay.

With respect to the U.V. erythema assay, it has been shown previously that the U.V. erythema condition is partially the result of a local release of prostaglandins derived oxidatively from arachidonic acid by the action of PG synthetases, e.g., cyclooxygenase. Therefore, pharmacological agents which inhibit the erythema are generally considered to be active topical anti-inflammatory agents.

Furthermore, anti-inflammatory agents which are not significantly systemically active are advantageous in the sense that they are not subject to the adverse effects, e.g., gastrointestinal ulcerations and bleeding that often plagued users of systemic NSAIDs (non-steroidal anti-inflammatory agents). Accordingly, an object of this invention is to provide novel phenylalkyldihydrobenzofuran derivatives and analogs as topical anti-inflammatory agents. These agents are useful in the treatment of dermal inflammatory conditions and prusitus such as sunburn, erythema, eczema, contact dermatitis, allergic dermatitis, psoriasis, and other skin diseases. They are also useful for topical application to prevent or treat peridontal diseases or to treat ocular inflammation.

Another object of this invention is to provide appropriate processes for the preparation of the subject novel compounds.

Still a further object of the present invention is to provide a pharmaceutically acceptable composition containing an effective amount of the active compound for the treatment of various inflammatory diseases especially those involving dermatological conditions.

Finally, it is the object of this invention to develop a method of treating inflammation especially dermal inflammation via the administration of a therapeutically effective amount of the novel compounds or pharmaceutically acceptable compositions thereof to a mammalian species in need of such treatment.

DETAILED DESCRIPTION OF THE INVENTION

A. Scope of the Invention

This invention relates to novel compounds of formula (I):

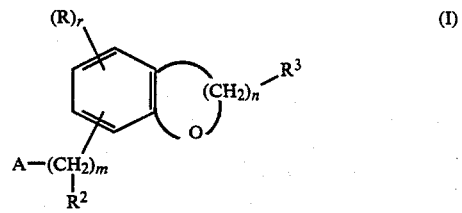

or a pharmaceutically acceptable salt thereof.

m is 1 to 4;
n is 2 or 3;
r is 1 to 3;
A is
(a) phenyl substituted with $(R^1)_q$ wherein q is an integer of 1 to 5 and when there are more than one $R^1$, $R^1$ can be the same or different from each other and is
  (1) hydrogen;
  (2) halo especially fluoro, chloro or bromo;
  (3) loweralkoxy especially $C_{1-6}$ alkoxy, e.g., methoxy, ethoxy, isopropoxy, t-butoxy or cyclohexyloxy, or —$OCH_2O$—;
  (4) lower alkylthio especially $C_{1-6}$ alkylthio, or $C_{1-6}$haloalkylthio e.g., methylthio, ethylthio, trifluoromethylthio or cyclohexylthio;
  (5) lower alkyl sulfinyl especially $C_{1-6}$ alkyl sulfinyl, e.g., methyl sulfinyl, i-propyl sulfinyl, and cyclopentyl sulfinyl;
  (6) lower alkyl sulfonyl especially $C_{1-6}$ alkyl sulfonyl such as methyl sulfonyl, ethyl sulfonyl and n-butyl sulfonyl;

(7) unsubstituted or substituted phenyl loweralkoxy such as benzyloxy;
(8) loweralkyl especially $C_{1-6}$ alkyl such as methyl, ethyl, propyl, t-butyl, pentyl, benzyl, cyclopropyl, cyclopentyl or cyclohexyl;
(9) loweralkenyl especially $C_{2-6}$ alkenyl, for example, vinyl, allyl, and buten-2-yl;
(10) lower alkanoyl especially $C_{1-6}$ alkanoyl such as formyl, acetyl or i-propanoyl;
(11) haloloweralkyl especially $C_{1-6}$ haloalkyl such as trifluoromethyl;
(12) —COOH;
(13) aryl especially phenyl or substituted phenyl, e.g., 4-methoxyphenyl, 2,4-difluorophenyl or 3-chlorophenyl; or
(14) aryloxy especially phenoxy;
(15) cyano;
(16) hydroxyloweralkyl especially hydroxy $C_{1-3}$ alkyl such as —CH$_2$OH, CH$_3$—CH(OH)—;
(17) halo loweralkanoyl especially halo$C_{1-6}$ alkanoyl eq. CF$_3$CO;
(18) heteroaryl as defined below;
(19) loweralkanoyloxy especially acetyloxy;
(20) hydroxy; or
(21) loweralkanoyl- or haloloweralkanoylloweralkyl;

(b) unsubstituted or substituted heteroaryl, for example:
(1) thienyl;
(2) benzothienyl;
(3) furyl;
(4) benzofuryl;
(5) pyrryl;
(6) indolyl;
(7) thiazolyl;
(8) benzothiazolyl;
(9) thiadiazolyl;
(10) benzothiadiazolyl;
(11) quinolyl;
(12) isoquinolyl;
(13) pyridyl;
(14) pyrazinyl;
(15) tetrazolyl;
(16) triazolyl; or
(17) imidazolyl; the heteroaryl above can be substituted with one or more of $R^1$, e.g., $C_{1-6}$ alkyl, $C_{1-6}$ alkanoyl, $C_{1-6}$ haloalkyl, halo, cyano, or hydroxy $C_{1-3}$ alkyl;
R, $R^2$ and $R^3$ independently are $R^1$.

In a preferred embodiment of this invention,
A is phenyl substituted with $(R^1)_q$ wherein q is 1 or 2 and $R^1$ is
(a) hydrogen;
(b) loweralkoxy;
(c) halo;
(d) lowerhaloalkyl,
(e) loweralkanoyl;
(f) hydroxyloweralkyl;
(g) hydroxy; or
(h) CN;
R is $R^1$ and R can be the same as or different from $R^1$;
$R^2$ is:
(a) phenyl;
(b) loweralkyl;
(c) loweralkanoyl; or
(d) hydroxyloweralkyl;
$R^3$ is H;
n is 2 or 3;
m is 1 to 4; and
r is 1.

In the even more preferred embodiment of the present invention, the compounds are of the following formulae:

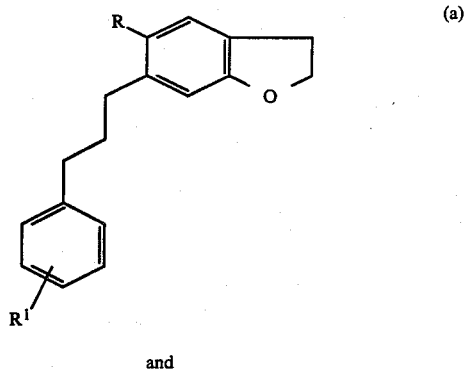

(a)

and

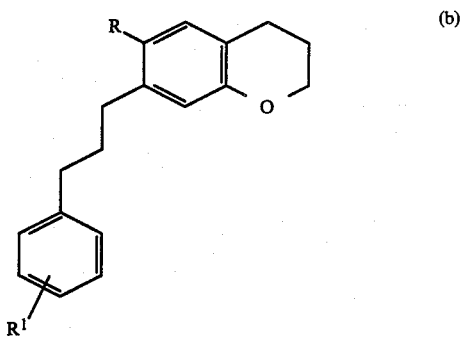

(b)

wherein $R^1$ is loweralkanoyl or hydroxyloweralkyl; R is $R^1$ and it can be the same as or different from $R^1$.

B. Preparation of the Compounds within the Scope of the Invention

The novel compounds of the present invention are prepared from known starting materials, for example:

Scheme (a)

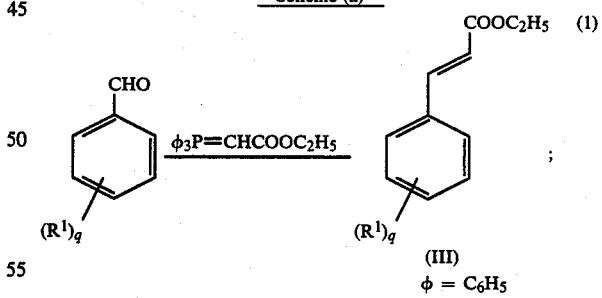

(1)

$\phi = C_6H_5$

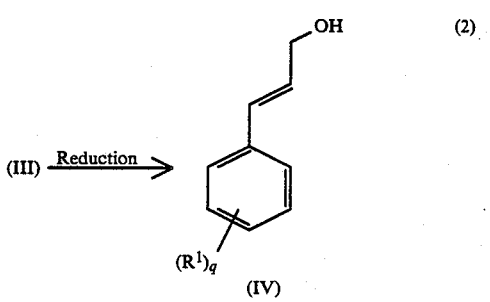

(2)

-continued
Scheme (a)
(3) (V) + (R)ᵣ— [aryl ether with (CH₂)ₙ—R³] —Alkylation→ (4)
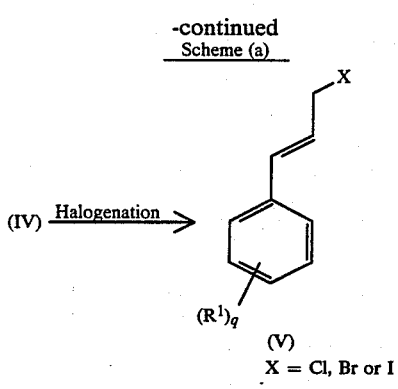
(V)
X = Cl, Br or I
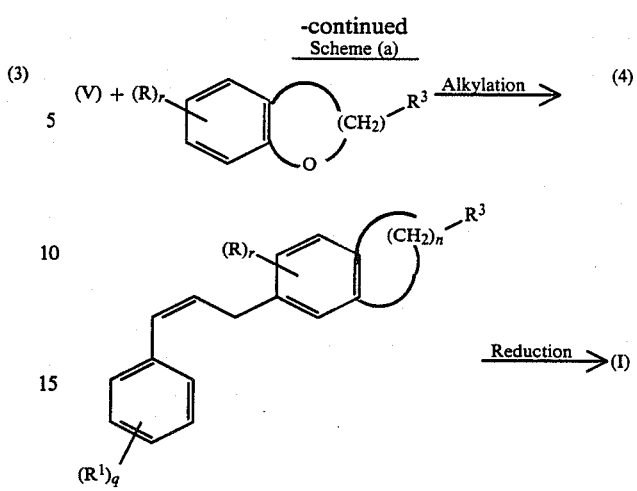
—Reduction→ (I)
Scheme (b)
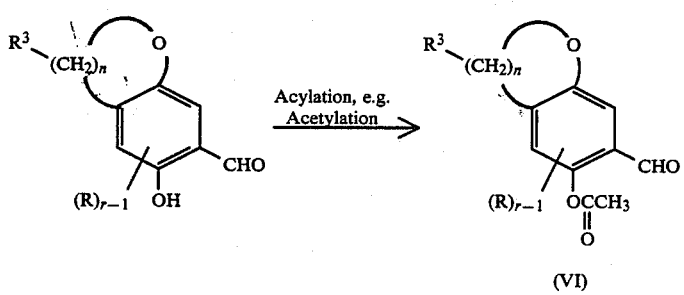
(1)
Aryl/heteroarylmethane (2)
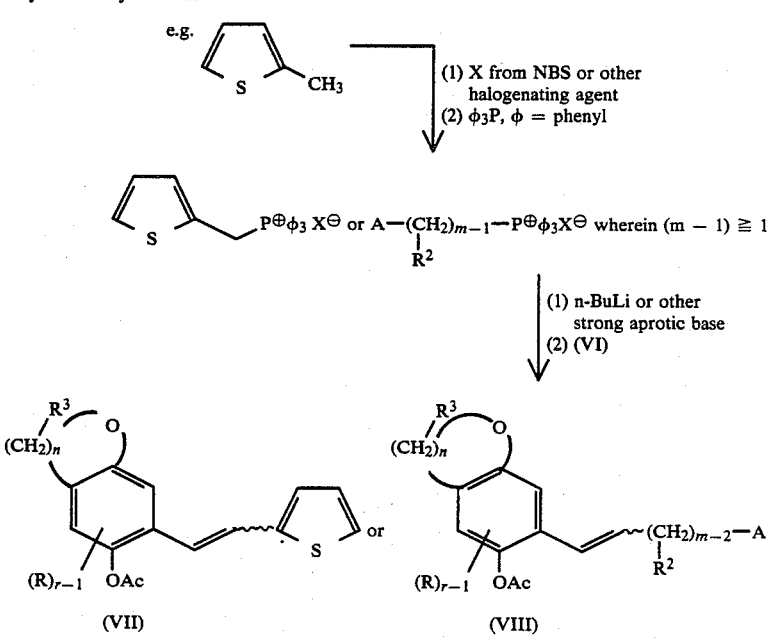

-continued
Scheme (b)
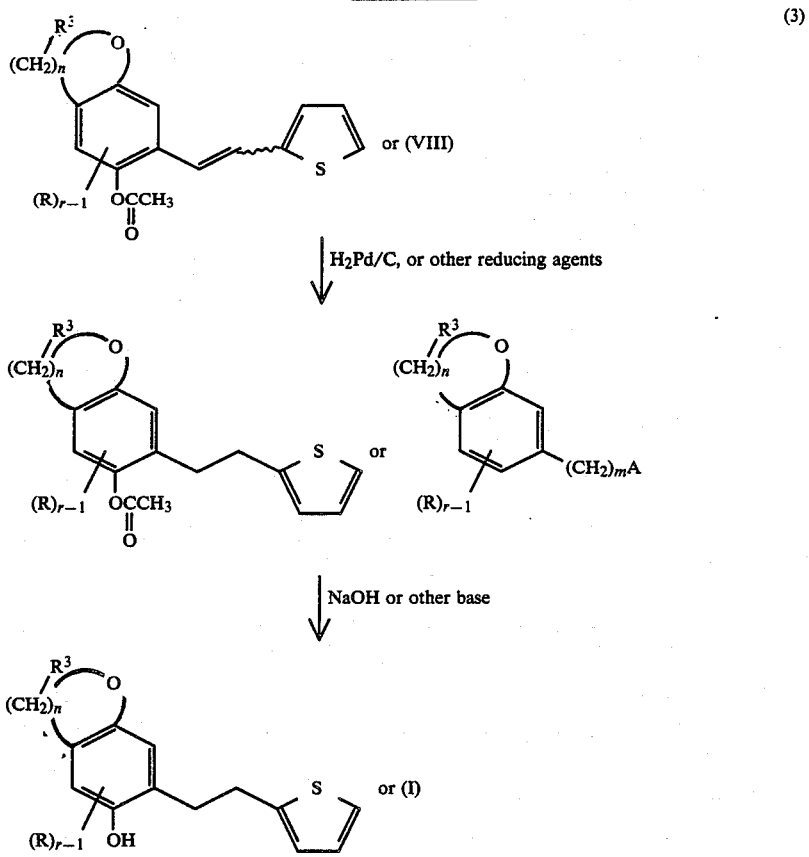
Scheme (c)
An Example for Preparing a Benzyl Derivative
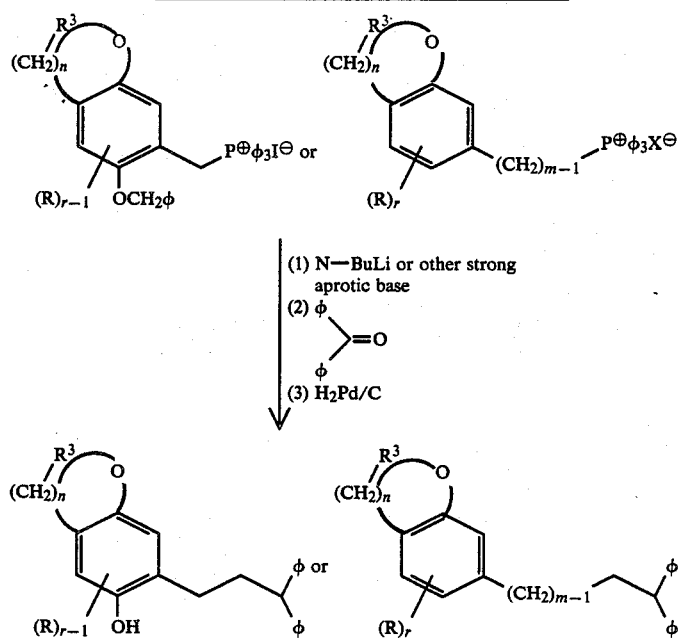
The procedures for preparing the starting materials such as cinnamylphenols are known and their preparations are similar to those disclosed in U.S. Pat. Nos. 3,745,222; 3,775,540; 3,777,039; 3,865,748; 3,936,393; 3,951,820; and 4,105,698.

C. Utility of the Subject Compounds of the Invention

This invention also relates to a method of treating inflammation especially topical inflammation in patients in need of such treatment. Generally, a sufficient amount of a compound of formula (I) or a pharmaceutical composition thereof, is administered to the patient as the active constituent.

The topical mouse ear assay (TME) was used to evaluate the novel compounds of the present invention for its effect on inflammatory responses elicited by topically applied phorbol myristate acetate (PMA) or topically applied archidonic acid (AA). The inflammatory responses may be in the form of edema (measured by wet weight); vascular permeability (measured by $^{125}$I-BSA accumulation); or PMN infiltration (measured by myeloperoxidase activity). A protocol of the assay and some results derived therefrom are summarized below.

Topical Mouse Ear Assay

Method: The right ears of mice (5 mice per group) were treated topically with either 5 μl PMA or 1000 μg AA alone or with the test compound in 25 μl of vehicle. The vehicle was water/pyridine/acetone (1:2:97). A control group of mice received the vehicle only. The mice were allowed food and water ad libitum during the treatment period; 2 hours for AA and 4 hours for PMA. The mice were sacrificed by ervical dislocation and a 6 mm diameter disc of tissue punched from both the treated and untreated ears. The tissue biopsies were immediately weighed and the weight increase of the treated ear relative to the weight of the untreated ear determined.

For the determination of vascular permeability, 1 μM $^{125}$I-bovine serum albumin ($^{125}$I-BSA) was administered in 0.5 ml phosphate buffered saline 15 min prior to the topical application. At the termination of the experiment, the amount of radioactivity in both the treated and untreated ear biopsies was determined and the increased amount of radioactivity in the treated tissue relative to the amount of radioactive in the untreated tissue determined.

As a measure of PMN infiltration, the amount of myeloperoxidase (MPO) activity in the same tissues was determined. The tissue biopsies were homogenized into 1 ml 0.5% hexadecyltrimethylammonium bromide and centrifuged for 45 min. at 1200×g. Aliquots 40 μl, of the supernatant phases were assayed for MPO activity by a colorimetric method devised by H. Dougherty for automated Titertek analysis. The MPO activity is expressed as the OD450 of the treated ear homogenate minus the OD450 of the non-treated ear homogenate.

All of the data are expressed as the mean±SEM, N=5 mice/group. The results are summarized below in Table I.

TABLE I

The effect of 6-(3-(4-acetylphenyl)propyl)-5-hydroxy-2,3-dihydrobenzofuran (Compound A) and 6-(3-(2-hydroxymethylphenyl)propyl)-5-hydroxy-2,3-dihydrobenzofuran (Compound B)

| Compound | ED$_{50}$ |
|---|---|
| Indomethacin | 308 |
| Compound A | 221 |
| Compound B | 20 |

For treatment of inflammation, fever or pain, the compounds of the invention are administered topically, by inhalation spray or rectally in dosage unit formulations containing conventional non-toxic pharmaceutically acceptable carriers, adjuvants and vehicles.

The pharmaceutical compositions containing the active ingredient may be in a form suitable for topical use, for example, aqueous or oily solutions or suspensions, dispersible powders or granules, tinctures, topical aerosol emulsions, creams, ointments, jellies, suppositories or the like. Compositions intended for topical use may be prepared according to any method known to the art for the manufacture of pharmaceutical compositions and such compositions may contain one or more active compounds.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyoxyethylene sorbitan monooleate. The said aqueous suspensions may also contain one or more preservatives, for example, ethyl, or n-propyl p-hydroxybenzoate.

Oily suspension may be formulated by suspending the active ingredient in a vegetable oil, for example, arachis oil, olive oil, sesame oil or coconut oil, or in a mineral oil such as liquid paraffin. The oily suspensions may contain a thickening agent, for example, beeswax, hard paraffin or cetyl alcohol. These compositions may be preserved by the addition of an antioxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above.

The pharmaceutical compositions of the invention may also be in the form of oil-in-water emulsions. The oily phase may be a vegetable oil, for example, olive oil or arachis oils, or a mineral oil, for example, liquid paraffin or mixtures of these. Suitable emulsifying agents may be naturally-occurring gums, for example, gum acacia or gum tragacanth, naturally-occurring phosphatides, for example, soy bean lecithin, and esters or partial esters derived from fatty acids and hexitol anhydrides, for example, sorbitan mono-oleate, and condensation products of the said partial esters with ethylene oxide, for example, polyoxyethylene sorbitan monooleate.

An ointment containing the pharmaceutical compositions of the present invention may be prepared, among other methods known in the art, by combining the active ingredient with a medium consisting of a glycol, a lower alkanol, and water; a gelling agent; and optionally an adjuvant such as diisopropyl adipate, diethyl sebacate, ethyl caproate and ethyl laurate. Suitable glycols include propylene glycol, butylene glycol, polyethylene glycol and the like. Generally, a caboxyvinyl polymer preneutralized with an organic amine such as diisopropyl amine and triethylamine, or a cellulose, e.g., hydroxyethyl cellulose, methyl cellulose, carboxymethyl cellulose, hydroxypropyl cellulose, is used as the gelling agent.

The compounds of the invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

Dosage levels of the order to 0.1 mg to 140 mg per kilogram of body weight per day are useful in the treatment of the above-indicated conditions (5 mg to 7 gms per patient per day). For example, inflammation is effectively treated by the administration from about 0.5 to 50 mg of the compound per kilogram of body weight per day (25 mg to 5 gms per patient per day). Advantageously, from about 2 mg to about 20 mg per kilogram of body weight per daily dosage produces highly effective results (50 mg to 1 gm per patient per day).

The amount of active ingredient that may be combined with the carrier materials to produce a single dosage form will vary depending upon the host treated and the particular mode of administration. Dosage unit forms will generally contain between from about 25 mg to about 1 g of active ingredient.

Particularly, for use in treatment of ophthalmic conditions including those associated with elevated intraocular pressure such as glacoma or other inflammation in the eye. The active compound can be administered topically or systemically when it is appropriate. The dose administered can be from as little as 0.1 to 25 mg or more per day, singly, or preferably on a 2 to 4 dose per day regimen although a single dose per day is satisfactory.

When given systemically, the drug can be given by any route, although the oral route is preferred. In oral administration the drug can be employed in any of the usual dosage forms such as tablets or capsules, either in a contemporaneous delivery or sustained release form. Any number of the usual excipients or tableting aids can likewise be included.

When given by the topical route, the active drug or an ophthalmologically acceptable salt thereof such as the sodium or potassium salt is formulated into an ophthalmic preparation. In such formulations, from 0.1% to 15% by weight can be employed. The objective is to administer a dose of from 0.1 to 10 mg per eye per day to the patient, with treatment continuing so long as the condition persists.

Thus, in an ophthalmic solution, insert, ointment or suspension for topical delivery, or a tablet, intramuscular, or intravenous composition for systemic delivery, the active medicament or an equivalent amount of a salt thereof is employed, the remainder being carrier, excipients, preservatives and the like as are customarily used in such compositions.

The active drugs of this invention are most suitably administered in the form of ophthalmic pharmaceutical compositions adapted for topical administration to the eye such as a suspension, ointment, or as a solid insert. Formulations of these compounds may contain from 0.01 to 15% and especially 0.5% to 2% of medicament. Higher dosages as, for example, about 10%, or lower dosages can be employed provided the dose is effective in reducing or controlling elevated intraocular pressure. As a unit dosage from between 0.001 to 10.0 mg, preferably 0.005 to 2.0 mg, and especially 0.1 to 1.0 mg of the compound is generally applied to the human eye, generally on a daily basis in single or divided doses so long as the condition being treated exists.

As with all medications, dosage requirements are variable and must be individualized on the basis of the disease and the response of the patient.

The pharmaceutical preparation which contains the active compound may be conveniently admixed with a non-toxic pharmaceutical organic carrier, or with a non-toxic pharmaceutical inorganic carrier. Typical of pharmaceutically acceptable carriers are, for example, water, mixtures of water and water-miscible solvents such as lower alkanols or aralkanols, vegetable oils, polyalkylene glycols, petroleum based jelly, ethyl cellulose, ethyl oleate, carboxymethylcellulose, polyvinylpyrrolidone, isopropyl myristate and other conventionally employed acceptable carriers. The pharmaceutical preparation may also contain non-toxic auxiliary substances such as emulsifying, preserving, wetting agents, bodying agents and the like, as for example, polyethylene glycols 200, 300, 400 and 600, carbowaxes 1,000, 1,500, 4,000, 6,000 and 10,000, antibacterial components such as quaternary ammonium compounds, phenylmercuric salts known to have cold sterilizing properties and which are non-injurious in use, thimerosal, methyl and propyl paraben, benzyl alcohol, phenyl ethanol, buffering ingredients such as sodium chloride, sodium borate, sodium acetates, gluconate buffers, and other conventional ingredients such as sorbitan monolaurate, triethanolamine, oleate, polyoxyethylene sorbitan monopalmitylate, dioctyl sodium sulfosuccinate, monothioglycerol, thiosorbitol, ethylenediamine tetraacetic acid, and the like. Additionally, suitable ophthalmic vehicles can be used as carrier media for the present purpose including conventional phosphate buffer vehicle systems, isotonic boric acid vehicles, isotonic sodium chloride vehicles, isotonic sodium borate vehicles and the like.

The pharmaceutical preparation may also be in the form of a solid insert such as one which after dispensing the drug remains essentially intact, or a biodegradable insert that either is soluble in lacrimal fluids, or otherwise disintegrates.

The following examples of ophthalmic formulations are given by way of illustration.

EXAMPLE A

| Compound A | 1 mg. | 15 mg. |
|---|---|---|
| Monobasic sodium phosphate.2H$_2$O | 10 mg. | 5 mg. |
| Dibasic sodium phosphate.12H$_2$O | 30 mg. | 15 mg. |
| Benzalkonium chloride | 0.1 mg. | 0.1 mg. |
| Water for injection q.s. ad. | 1.0 ml. | 1.0 ml. |

Compound A, phosphate buffer salts, and benzalkonium chloride are added to and dissolved in water. The pH of the composition is adjusted to 6.8 and diluted to volume. The composition is rendered sterile by ionizing radiation.

EXAMPLE B

| A Compound of formula (I) | 5 mg. |
|---|---|
| petrolatum q.s. ad. | 1 gram |

The active compound and the petrolatum are aseptically combined.

EXAMPLE C

| A Compound of formula (I) | 1 mg. |
|---|---|
| Hydroxypropylcellulose q.s. | 12 mg. |

Ophthalmic inserts are manufactured from compression molded films which are prepared on a Carver Press by subjecting the powdered mixture of the above ingredients to a compressional force of 12,000 lbs. (gauge) at 300° F. for one to four minutes. The film is cooled under pressure by having cold water circulate in the platen. Ophthalmic inserts are then individually cut from the film with a rod-shaped punch. Each insert is placed into a vial, which is then placed in a humidity cabinet (88% R. H. at 30° C.) for two to four days. After removal from the humidity cabinet, the vials are stoppered and then capped. The vials containing the hydrate insert are then autoclaved at 250° F. for ½ hour.

EXAMPLE D

| A Compound of formula (I) | 1 mg. |
|---|---|
| Hydroxypropyl cellulose q.s. ad. | 12 mg. |

Ophthalmic inserts are manufactured from a solvent cast film prepared by making a viscous solution of the powdered ingredients listed above using methanol as the solvent. The solution is placed on a Teflon plate and allowed to dry at ambient conditions. After drying, the film is placed in an 88% R. H. cabinet until it is pliable. Appropriately sized inserts are cut from the film.

EXAMPLE E

| A Compound of formula (I) | 1 mg. |
|---|---|
| Hydroxypropylmethyl cellulose q.s. ad. | 12 mg. |

Ophthalmic inserts are manufactured from a solvent cast film which is prepared by making a viscous solution of the powdered blend of the above ingredients using a methanol/water solvent system (10 ml. methanol is added to 2.5 g. of the powdered blend, to which 11 ml. of water (in three divided portions) is added. The solution is placed on a Teflon plate and allowed to dry at ambient conditions. After drying, the film is placed in an 88% R. H. cabinet until it is pliable. Appropriately sized inserts are then cut from the film.

EXAMPLE F

| A Compound of formula (I) | 1 mg. |
|---|---|
| Hydroxypropylmethyl cellulose q.s. ad. | 12 mg. |

Ophthalmic inserts are manufactured from compression molded films which are prepared on a Carver Press by subjecting the powdered mixture of the above ingredients to a compressional force of 12,000 lbs. (gauge) at 350° F. for one minute. The film is cooled under pressure by having cold water circulate in the platen. Ophthalmic inserts are then individually cut from the film with a punch. Each insert is placed into a vial, which is then placed in a humidity cabinet (88% R. H. at 30° C.) for two to four days. After removal from the humidity cabinet, the vials are stoppered and then capped. The vials containing the hydrated insert are then autoclaved at 250° F. for one-half hour.

It is highly preferred that the solid inserts of this invention are available for use by the patient in a pathogen free condition. Thus, it is preferred to sterilize the inserts and to insure against recontamination, the sterilization is preferably conducted after packaging. The best mode of sterilizing is to employ ionizing radiation including radiation emanating from Cobalt 60 or high energy electron beams.

EXAMPLE G

The following materials are mixed in a 1250 ml bottle: 24 g of Compound A which is a sufficient amount of medicament to result in a concentration of 10 mg per ml in the final samples, allowing for previously established 3.0% average; 0.4 g sodium bisulfite, 12 g NaCl, and 28 ml water (at 180° F.). This mixture, (I), is autoclaved for 30 minutes at 121° C. under 15 psi. Separately, 3 g of hydroxyethylcellulose in 720 ml of water (II) and 0.4 g of lecithin in 80 ml of water (III) were autoclaved for 30 minutes at 121° C. Then, (III) is admixed with (I) for 2 hours, and the resultant mixture poured into (II). Another mixture (IV) is prepared from 20 g of sorbitol, 2.36 ml of benzalkonium chloride, 10 g of disodium edetate, and water to give a final solution volume of 900 ml. Then, (IV) is added to the mixture of (I), (II), and (III) in sufficient quantity to give 1.8 l. overall. The 1.8 l. mixture of I, II, III, and IV is then taken and homogenized using a homogenizer at 2000 psig. Stock solutions are then prepared for polyoxyethylene (20) sorbitan monooleate by dissolving 3 g of the material in 100 ml of water, and of benzyl alcohol/β-phenyl-ethyl alcohol by admixing 50 ml of each alcohol. Varying quantities of the two stock solutions are then added to four 90 ml aliquots of the homogenized mixture of (I), (II), (III), and (IV) prepared as described above, together with sufficient water to give a total of 100 ml for each of four different samples.

Other formulations, in an oil vehicle and an ointment are exemplified in the following examples.

EXAMPLE H

Solution Composition

| Compound B | 0.1 mg. |
|---|---|
| Peanut oil q.s. ad. | 0.10 mg. |

The solution is rendered sterile by filtration through a sterilizing filter.

EXAMPLE I

| Compound A | 0.5 gm. |
|---|---|
| Petrolatum q.s. ad. | 1 gram |

The compound and the petrolatum are aseptically combined.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

Set forth below are some illustrative topical formulations containing a selected active compound of the instant invention.

| Formulation Number 1 - Solution |
| --- |
| Distilled water qs to 100% |
| Procedure: Dissolve compound (A) in enough water to make 100%. Filter the solution. Apply to the affected area. |

| Formulation Number 2 - Tincture | |
| --- | --- |
| Alcohol U.S.P. | 50% |
| Water qs to 100% | |

Procedure: Dissolve compound (A) in the alcohol. Add sufficient water to make 100%. Filter and apply to affected area.

| Formulation Number 3 - Topical Aerosol | |
| --- | --- |
| Alcohol U.S.P. | 5% |
| Isopropylmyristate | 5% |

Conventional halogenated hydrocarbon propellant qs 100% e.g., Freon 11(trichlorofuluromethane), Freon 12(dichlorodifluoromethane), Freon 14 (carbon tetrafluoride), Freon C 318 (Octafluorocyclobutane), Freon 114(Cryofluorane), etc.

Procedure: Dissolve Compound (A) in the alcohol and isopropylmyristate. Add sufficient halogenated propellant and introduce into conventional aerosol containers either by pressure or by cold filing. Apply to affected area.

| Formulation Number 4 - Ointment | |
| --- | --- |
| Petrolatum U.S.P. qs to | 100% |

Procedure: Heat the petrolatum to 60° C. Add compound (A) and stir until thoroughly dispersed. Cool to room temperature. Apply to affected area.

Set forth below are some illustrative examples for the preparation of the compounds of the present invention:

EXAMPLE 1

6-(3-(2-hydroxymethyl-phenyl)propyl)-5-hydroxy-2,3-dihydrobenzofuran 6-(3-(2-hydroxymethylphenyl)-trans-prop-2-enyl)-5-hydroxy-2,3-dihydrobenzofuran (2.82 g; 0.01 moles) was dissolved in acetic acid (35 ml) and ethyl alcohol (10 ml) and hydrogenated at 40 psi at room temperature using $PtO_2$ (0.30 g) as a catalyst. The reduction was complete in approximately 3 minutes with a slight exotherm. The catalyst was removed via suction filtration through a bed of celite. The bed was washed with ethyl alcohol (2×10 ml) and the filtrate was relieved of solvent in vacuo to afford a crude gum. The gum was dissolved in ethyl ether (50 ml) and was washed sequentially with brine (2×50 ml) and saturated $NaHCO_3$ solution (2×50 m). The organic layer was dried over $MgSO_4$, filtered, and the filtrate evaported in vacuo to yield a crude solid. Recrystallization from ethyl acetate/n-hexane produced 6-(3-(2-hydroxymethyl-phenyl)-propyl)-5-hydroxy-2,3-dihydrobenzofuran as white needles (1.4 g, 49%, m.p. 110°–111.5° C.).

Calc'd for $C_{18}H_{20}O_3$: C, 76.03; H, 7.09; Found: C, 75.84; H, 7.12.

EXAMPLE 2

6-(3-(4-acetyl-phenyl)-propyl)-5-hydroxy-2,3-dihydrobenzofuran

An isomeric mixture (1:1) of 6-(3-(4-acetyl-phenyl)-propen-2 or 1-yl)-5-hydroxy-2,3-dihydrobenzofuran (740 mg, 2.5 mmoles) was hydrogenated at 40 psi in acetic acid (10 ml)/ethyl alcohol (20 ml)/$PtO_2$ (100 mg) until the reduction of the double bond was complete. The catalyst was removed via suction filtration through a bed of celite, and the filter cake washed with ethyl alcohol. The filtrate was concentrated in vacuo to afford a crude oil. The oil was partitioned in $Et_2O$(25 ml)/$H_2O$ (20 ml) and a sufficient amount of sodium bicarbonate powder was added to neutralize any residual acetic acid. The layers were separated and the organic phase washed with saturated $NaHCO_3$ solution (1×20 ml) and then brine (2×20 ml).

The ether layer was dried over $MgSO_4$, filtered and the filtrate evaporated in vacuo to produce a crude gum. High performance liquid chromatography (HPLC) using on EtoAc/hexane (30%:70%) mobile phase on silica gel was used to separate the title compound from its 1-hydroxyethyl analogs resulting from the reduction of the acetyl group. The isolated product was recrystallized from EtOAc/n-hexane to afford phenylalkyl-2,3-dihydrobenzofurans and analogs useful as anti-inflammatory agents as white crystals. m.p. 125°–126.5° C.

Calc'd for $C_{19}H_{20}O_3$: C, 77.00; H, 6.8; Found: C, 77.07; H, 6.85.

Similarly, HPLC fractions containing the 1-hydroxyethyl analog was recrystallized to afford 6-(3-(4-(1-hydroxyethyl)-phenyl)-propyl)-5-hydroxy-2-3-dihydrobenzofuran, m.p. 104°–105° C.

Calc'd for $C_{19}H_{22}O_3$: C, 76.48; H 7.43, Found: C, 76.32; H, 7.45.

EXAMPLE 3

6-(2-(1-methyl-imidazol-2-yl)ethyl)-5-hydroxy-2,3-dihydrobenzofuran

Step A: Preparation of 5-benzyloxy-2,3-dihydrobenzofuran-6-carboxaldehyde

A 2-liter, 3-neck flask equipped with a nitrogen inlet, internal thermometer, mechanical stirrer, and reflux condenser was charged with 5-hydroxy-2,3-dihydrobenzofuran-6-carboxaldehyde (50.00 g; 0.30 moles), benzylbromide (38.6 ml, 0.34 moles), and crushed anhydrous $K_2CO_3$ (165.84 g, 1.20 moles). The reaction mixture was refluxed for 16 hours, cooled to room termperature and suction filtered. The filtrate was concentrated in vacuo to afford a yellow solid. The solid was dissolved in methylene chloride (600 ml) and washed sequentially with 0.5 N sodium hydroxide solution (3×250 ml) and brine (2×250 ml). The organic phase was dried over $MgSO_4$, suction filtered, and the filtrate concentrated in vacuo to yield a crude solid (85 g). The solid was dissolved in methylene chloride (300 ml)/n-hexane (200 ml), treated with charcoal and suction filtered through a bed of celite. The filtrate was evaporated in vacuo to approximately 300 ml and slowly cooled to 0° C. to produce yellowish flat needles (60 g, 78%).

Step B: Preparation of 5-benzyloxy-6-hydroxymethyl-2,3-dihydobenzofuran

A flamed dried, $N_2$ purged 1-liter, 3-neck flask equipped with a dropping funnel mechanical stirrer, and thermometer was charged with 5-benzyloxy-2,3-dihydrobenzofuran-6-carboxaldehyde (30.00 g, 0.12 moles) and anhydrous toluene (150 ml). The resultant yellow solution was cooled to $-65°$ C. and with efficient stirring a diisobutylaluminum hydride solution in toluene (77 ml of a 25 wt. %) was added dropwise over 30 minutes. Upon complete addition, the reaction mixture was allowed to warm to room temperature and stirred 1 hour more. The reaction mixture was poured slowly into 2N HCl (300 ml) and crushed ice (400 ml) with rapid stirring. The quenched mixture was extracted sequentially with $Et_2O$ (2×300 ml) and EtoAC (2×200 ml). The combined organic layers were washed with brine (2×300 ml), dried over $MgSO_4$, filtered, and the filtrate concentrated in vacuo to afford 5-benzyloxy-6-hydroxymethyl-2,3-dihydobenzofuran as a white precipitate (30.0 g, 97.5%).

Step C: Preparation of 5-benzyloxy-6-(methanesulfonyloxymethyl)-2,3-dihydrobenzofuran A flame dried 1-liter, 3-neck flask fitted with a dropping funnel, mechanical stirrer, $N_2$ inlet, and an internal thermometer was charged with 5-benzyloxy-6-hydroxymethyl-2,3-dihydrobenzofuran (28.90 g, 0.11 moles), methylene chloride (250 ml) and triethylamine (16 ml, 0.11 moles). The reaction mixture was chilled to 10° C. and methanesulfonyl chloride (8.9 ml, 0.11 mole) was added dropwise, while maintaining an internal reaction temperature of 10° C. The resultant yellow-green mixture was warmed to room temperature and stirred for 15 hours. Water (100 ml) was added to the reaction, the layers partitioned and separated. The organic phase was washed sequentially with saturated sodium bicarbonate solution (2×100 ml) and brine (1×100 ml) to remove some greenish color. The yellow organic layear was dried over $MgSO_4$, suction filtered and the filtrate concentrated in vacuo to afford 5-benzyloxy-6-methanesulfonyloxymethyl)-2,3-dihydrobenzofuran a yellow precipitate (33.0 g, 88%). The crude product was used in the next step without further purification which was not necessary for the subsequent reaction.

Step D: Preparation of 5-benzyloxy-6-iodomethyl-2,3-dihydrobenzofuran

A flame dried, $N_2$ purged 1-liter, 3-neck round bottom flask equipped with an internal thermometer and mechanical stirrer was charged with 5-benzyloxy-6-(methanesulfonyloxymethyl)-2,3-dihydrobenzofuran (30.60 g, 0.10 moles) and anhydrous acetone (250 ml). The resultant solution was cooled to 0° C. and with efficient stirring sodium iodide (59.90 g, 0.40 moles) in acetone (150 ml) was added in one portion. The reaction mixture was stirred at room temperature for 72 hours and then suction filtered through a bed of celite. The filtrate was concentrated in vacuo to afford the crude product. This was dissolved in ethyl ether (400 ml) and water (200 ml), the layers partitioned, and separated. The organic phase was washed with saturated $NaHSO_3$ solution (2×200 ml) and water (1×200 ml), dried over $MgSO_4$, suction filtered, and the filtrate concentrated in vacuo to yield 5-benzyloxy-6-iodomethyl-2,3-dihydrobenzofuran as a yellow solid (33.0 g, 98%).

Step E: Preparation of 5-benzyloxy-2,3-dihydrobenzofuran-6-yl methenyltriphenylphosphonium iodide A flame dried 1-liter, 3-neck flask fitted with a mechanical stirrer, nitrogen inlet, reflux condenser and internal thermometer was charged with 5-benzyloxy-6-iodomethyl-2,3-dihydrobenzofuran (25.0 g, 0.7 moles) and anhydrous benzene (250 ml). With efficient stirring, to this solution was added, dropwise, a solution of triphenylphosphine (18.4 g, 0.7 moles) in benzene (100 ml). Upon complete addition, the reaction mixture was refluxed for ½ hour, whereupon a solution formed. This solution was cooled to 0° C. and a fine white precipitate formed which was isolated by suction filtration. The filter cake was washed with ethyl ether and dried in a vacuum oven under a nitrogen purge. The phosphonium salt was of sufficent purity for the next reaction (41.0 g, 96.0%).

Step F: Preparation of cis- and trans-isomers of 1-(5-benzyloxy-2,3-dihydrobenzofuran-6-yl)-2(1-methyl-imidazol-2-yl)ethene A flame dried, $N_2$ purged, 100 ml round bottom flask equipped with a dropping funnel, thermometer and magnetic stirrer was charged with 5-(benzyloxy)-2,3-dihydrobenzofuran-6-yl methyltriphenylphosphonium iodide (3.0 g, 4.8 mmoles) and anhydrous THF (15 ml). The suspension was cooled to $-20°$ C. and a 1.55 M solution of n-butyllithium (3.1 ml, 4.8 mmoles) was added dropwise, while maintaining an internal reaction temperature of $-20°$ C. The suspension became a red solution and stirring was continued 1 hour more at 0° C. The reaction mixture was chilled to $-25°$ C. and a solution of 1-methylimidazole-2-carboxaldehyde (525 mg, 4.8 mmoles) in THF. (10 ml) was added dropwise over 5 minutes. The reaction mixture was allowed to warm to room temperature and stir for 12 hours. It was then cooled to 0° C. and water (1.0 ml) added. It was further stirred for ½ hour whereupon the solvent was removed in vacuo to afford the crude product. The crude product was dissolved in ethyl ether (20 ml) and water (20 ml). The layers were partitioned and separated. The organic phase was washed with water (2×20 ml), dried over $MgSO_4$, suction filtered, and the filtrate concentrated in vacuo to yield a crude yellow oil. Further purification was achieved by high performance liquid chromatography to produce approximately a 1:1 ratio of cis and trans isomers of 1-(5-benzyloxy-2,3-dihydrobenzofuran-6-yl)-2-(1-methyl-imidazol-2-yl)ethene (600 mg, 38%).

Step G: Preparation of 6-(2-(1-methylimidazol-2-yl)ethyl)-5-hydroxy-2,3-dihydrobenzofuran Approximately a 1:1 ratio of cis and trans isomers of 1-(5-benzyloxy-2,3-dihydrobenzofuran-6-yl)-2-(1-methylimidazol-2-yl)ethene (104 mg, 0.3 mmoles) was hydrogenated in ethyl alcohol (15 ml) at room temperature using 10% Pd/C (15 mg) as a catalyst which was removed by suction filtration of the reaction mixture through a bed of celite. The catalyst bed was washed with ethyl alcohol (2×10 ml) and the filtrate was evaporated in vacuo to afford a white solid. Recrystallization from methlene chloride/n-hexane produced 6-(2-(1-methylimidazol-2-yl)ethyl)-5-hydroxy-2,3-dihydrobenzofuran as fine white crystals (60 mg, 79%). m.p. 190°–191° C.

EXAMPLE 4

5-Hydroxy-2,3-dihydro-6-(2-(2-thienyl)ethyl)-benzofuran

Step A: Preparation of 5-acetoxy-2,3-dihydrobenzofuran-6-carboxaldehyde

A solution of 5-hydroxy-2,3-dihydrobenzofuran-6-carboxaldehyde (5.0 g, 0.030 mol) in pyridine (10 ml) was cooled to an internal temperature of −5° C. Acetic anhydride (3.2 g, 0.03 mol) was added dropwise. The cooling bath was removed and the mixture was allowed to stir under nitrogen for 18 hours. The reaction was quenched into water (50 ml) at which time the product crystallized and was collected by filtration. The product was dissolved in methylene chloride (100 ml) and was washed with water (25 ml), saturated sodium bicarbonate (25 ml) saturated sodium chloride (25 ml), dried (MgSO$_4$) and concentrated to a dark oil which solidified on standing. The product was ground, washed with ethyl ether and dried to afford 5-acetoxy-3,4-dihydrobenzofuran-6-carboxaldehyde (4.6 g, 74%). m.p. 68°–70° C.

Step B: Preparation of (2-thienyl)methyl triphenylphosphonium bromide

A mixture of 2-methylthiophene (10 g, 0.10 mol) and N-bromosuccinimide (18 g, 0.10 mol) in carbon tetrachloride (100 ml) was heated to reflux under nitrogen. Benzoyl peroxide (50 mg) was added and the mixture was refluxed for 3 hours. After cooling to room temperature the reaction was filtered and concentrated to a dark oil. The crude 2-bromomethylthiophene and triphenylphosphine (29 g, 0.011 mol) were dissolved in tetrahydrofuran (170 ml) under nitrogen and heated to reflux for 4 hours and then cooled to room temperature for precipitation. The product was collected by filtration, washed with ethyl ether (4×15 ml) and dried to afford (2-thienyl)methyl triphenylphosphonium bromide (35 g, 80%). m.p. 250° C.

Step C: Preparation of 1-(5-acetoxy-2,3-dihydrobenzofuran-6-yl)-2-(2-thienyl)ethene (cis- and trans-isomers)

A mixture of (2-thienyl)methyl triphosphonium bromide (22 g, 0.054 mol) in tetrahydrofuran (200 ml) was cooled to an internal temperature of 8° C. under nitrogen and a solution of n-butyllithium (1.55M in hexane, 33 ml, 5.5 mol) was added dropwise. The resulting mixture was stirred for 10 minutes then 5-acetoxy-2,3-dihydrobenzofuran-6-carboxaldehyde (7.0 g, 0.034 mol) was added portionwise. The ice bath was removed and the reaction was allowed to stir for 3 days. After filtration and concentration the crude product was purified by chromatography over silica gel (hexane/ethyl acetate, 80/20 as eluent) to afford a 1:1 mixture of cis- and trans-isomers of 1-(5-acetoxy-2,3-dihydrobenzofuran-6-yl)-2-(2-thienyl)ethene (0.55 g, 39%).

Step D: Preparation of 5-Hydroxy-2,3-dihydro-6-(2-(2-thienyl)-ethyl-benzofuran A mixture of 1-(5-acetoxy-2,3-dihydrobenzofuran-6-yl)-2-(2-thienyl)ethene (0.55 g, 0.0019 mol), in ethanol (20 ml) and 12N HCl (0.5 ml) was hydrogenated at 40 psi using 10% Pd/C (0.55 g) as catalyst. After filtration and concentration the crude 5-acetoxy-6-(2-(2-thienyl)ethyl)-2,3-dihydrobenzofuran was dissolved in methylene chloride (20 ml) and washed with saturated sodium bicarbonate (2×10 ml) saturated sodium chloride (10 ml) and concentrated. The resulting yellow oil was dissolved in ethanol (10 ml) and 50% NaOH (0.2 ml). The mixture was allowed to stir for ½ hour at room temperature and was concentrated. The crude product was dissolved in methylene chloride (20 ml) and washed with 10% acetic acid (10 ml), saturated sodium carbonate (10 ml), saturated sodium chloride (10 ml). The combined organic layers were dried (MgSO$_4$), and concentrated to a dark oil. Purification by chromatography over silica gel (hexane/ethyl acetate, 90/10, as eluent) afforded 5-hydroxy-6-(2-(2-thienyl)ethyl)-2,3-dihydrobenzofuran (66 mg, 13%). m.p. 79°–85° C.

EXAMPLE 5

6-(2-(2,2-diphenyl)ethyl)-5-hydroxy-2,3-dihydrobenzofuran

A mixture of (5-benzyloxy-2,3-dihydro-benzofuran-6-yl)methyl triphenylphosphine iodide (2.0 g, 0.0033 mol) in tetrahydrofuran (20 ml) was cooled to an internal temperature of 5° C. under nitrogen and a solution of n-butyllithium (1.55M in hexane, 1.9 ml, 0.0030 mol) was added dropwise. The resulting mixture was stirred for 10 minutes then benzophenone (0.47 g, 0.0030 mol) was added portionwise. The ice bath was removed and the reaction was allowed to stir for 18 hours, then heated to reflux for 4 hours. The reaction mixture was concentrated to a dark oil which was dissolved in ethyl acetate (20 ml), washed with water (10 ml), saturated sodium chloride (10 ml). The combined organic layers were dried (MgSO), concentrated then chromatographed over silica gel (hexane/ethyl acetate, 90/10, an eluent) to afford 1-(5-benzyloxy-2,3-dihydrobenzofuran-6-yl)-2,2-diphenyl-ethene (0.27 g, 22%).

The material was suspended in ethanol (10 ml) and 12N HCl (0.3 ml) and hydrogenated at 40 psi using 10% Pd/C as catalyst. After filtration and concentration the crude product was purified by chromatography over silica gel (hexane/ethyl acetate, 90/10, an eluent) to afford 6-(2-(2,2-diphenyl)ethyl)-5-hydroxy-2,3-dihydrobenzofuran (0.12 g, 13%). m.p 153°–157° C.

What is claimed is:
1. A compound of the formula:

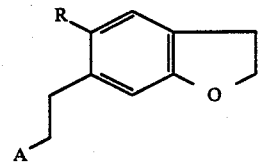

or a pharmaceutically acceptable salt thereof wherein
A is unsubstituted or substituted heteroaryl selected from a group consisting of:
(1) thienyl;
(2) benzothienyl; p1 (3) furyl;
(4) benzofuryl;
(5) pyrryl;
(6) tetrazolyl; or
(7) imidazolyl;
the heteroaryl above being substituted with one or more of R$^1$ wherein R$^1$ is
(1) hydrogen;

(2) halo;
(3) loweralkoxy;
(4) lower alkylthio;
(5) lower alkyl sulfinyl;
(6) lower alkyl sulfonyl;
(7) loweralkyl;
(8) lower alkanoyl;
(9) haloloweralkyl;
(10) phenyl;
(11) hydroxyloweralkyl;
(12) halo loweralkanoyl;
(13) loweralkanoyloxy;
(14) hydroxy; or
(15) loweralkanoyl- or haloloweralkanoylloweralkyl; and R is
(1) hydroxy;
(2) loweralkoxy;
(3) phenylloweralkoxy; or
(4) loweralkanoyloxy.

2. The compound of claim 1 wherein
R is loweralkoxy or hydroxy;
A is unsubstituted or substituted heteroaryl selected from a group consisting of
(1) thienyl;
(2) benzothienyl; or
(3) imidazolyl, 3. The compound of claim 1 wherein
R is methoxy or hydroxy;
A is

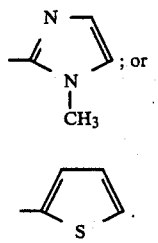

4. A pharmaceutical composition for treating topical inflammation comprising a pharmaceutical carrier and an effective amount of a compound of the formula:

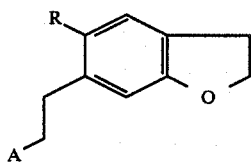

or a pharmaceutically acceptable salt thereof wherein
A is unsubstituted or substituted heteroaryl selected from a group consisting of:
(1) thienyl;
(2) benzothienyl;
(3) furyl;
(4) benzofuryl;
(5) pyrryl;
(6) tetrazolyl; or
(7) imidazolyl;
the heteroaryl above being substituted with one or more of $R^1$ wherein $R^1$ is
(1) hydrogen;
(2) halo;
(3) loweralkoxy;
(4) lower alkylthio;
(5) lower alkyl sulfinyl;
(6) lower alkyl sulfonyl;
(7) loweralkyl;
(8) lower alkanoyl;
(9) haloloweralkyl;
(10) phenyl;
(11) hydroxyloweralkyl;
(12) halo loweralkanoyl;
(13) loweralkanoyloxy;
(14) hydroxy; or
(15) loweralkanoyl- or haloloweralkanoylloweralkyl; and R is
(1) hydroxy;
(2) loweralkoxy;
(3) phenylloweralkoxy; or
(4) loweralkanoyloxy.

5. The composition of claim 4 wherein
A is unsubstituted or substituted heteroaryl selected from a group consisting of
(1) thienyl;
(2) benzothienyl; or
(3) imidazolyl;
R is loweralkoxy or hydroxy.

6. The composition of claim 4 wherein
R is methoxy or hydroxy;
A is

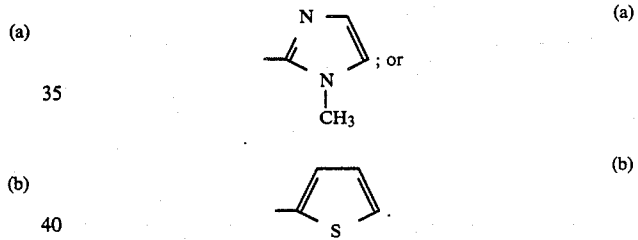

7. A method of treating topical inflammation comprising the administration to a mammalian species in need of such treatment a therapeutically effective amount of compound of the formula:

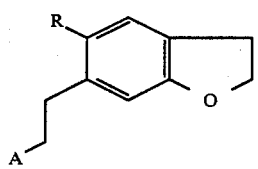

or a pharmaceutically acceptable salt thereof wherein
A is unsubstituted or substituted heteroaryl selected from a group consisting of:
(1) thienyl;
(2) benzothienyl;
(3) furyl;
(4) benzofuryl;
(5) pyrryl;
(6) tetrazolyl; or
(7) imidazolyl;
the heteroaryl above being substituted with one or more of $R^1$ wherein $R^1$ is
(1) hydrogen;

(2) halo;
(3) loweralkoxy;
(4) lower alkylthio;
(5) lower alkyl sulfinyl;
(6) lower alkyl sulfonyl;
(7) loweralkyl;
(8) lower alkanoyl;
(9) haloloweralkyl;
(10) phenyl;
(11) hydroxyloweralkyl;
(12) halo loweralkanoyl;
(13) loweralkanoyloxy;
(14) hydroxy; or
(15) loweralkanoyl- or haloloweralkanoylloweralkyl; and R is
(1) hydroxy;
(2) loweralkoxy;
(3) phenylloweralkoxy; or
(4) loweralkanoyloxy.

8. The method of treatment of claim 7 wherein R is loweralkoxy or hydroxy;
A is unsubstituted or substituted heteroaryl selected from a group consisting of
(1) thienyl;
(2) benzothienyl; or
(3) imidazolyl.

9. The method of treatment of claim 7 wherein R is methoxy or hydroxy;
A is

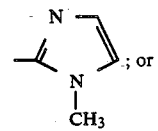 (a)

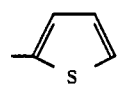 (b)

* * * * *